US010168260B2

(12) United States Patent
White et al.

(10) Patent No.: US 10,168,260 B2
(45) Date of Patent: Jan. 1, 2019

(54) SELF-FILLING SOIL PROCESSING CHAMBER WITH DYNAMIC EXTRACTANT VOLUME

(71) Applicant: WINFIELD SOLUTIONS, LLC, Shoreview, MN (US)

(72) Inventors: Justin S. White, Palo Alto, CA (US); Stephen D. Prouty, San Jose, CA (US); Michael J. Preiner, Seattle, WA (US); Nicholas C. Koshnick, Palo Alto, CA (US)

(73) Assignee: WINFIELD SOLUTIONS, LLC, Shoreview, MN (US)

( * ) Notice: Subject to any disclaimer, the term of this patent is extended or adjusted under 35 U.S.C. 154(b) by 0 days.

(21) Appl. No.: 15/682,468

(22) Filed: Aug. 21, 2017

(65) Prior Publication Data

US 2017/0356828 A1   Dec. 14, 2017

Related U.S. Application Data

(63) Continuation of application No. 15/075,649, filed on Mar. 21, 2016, now Pat. No. 9,739,693, which is a
(Continued)

(51) Int. Cl.
*G01N 1/38* (2006.01)
*G01N 19/10* (2006.01)
(Continued)

(52) U.S. Cl.
CPC ............... *G01N 1/38* (2013.01); *G01N 15/06* (2013.01); *G01N 19/10* (2013.01); *G01N 21/25* (2013.01);
(Continued)

(58) Field of Classification Search
CPC .......... G01N 1/38; G01N 15/06; G01N 19/10; G01N 21/25; G01N 33/24
See application file for complete search history.

(56) References Cited

U.S. PATENT DOCUMENTS

| 1,840,100 A | 1/1932 | Jacobsen |
| 3,193,355 A | 7/1965 | Fuhrmann |
(Continued)

FOREIGN PATENT DOCUMENTS

EP   0802406 A2   10/1997

OTHER PUBLICATIONS

U.S. Appl. No. 13/797,546, filed Mar. 12, 2013, Notice of Allowance, dated Dec. 23, 2015.
(Continued)

*Primary Examiner* — Hezron E Williams
*Assistant Examiner* — David Z Huang
(74) *Attorney, Agent, or Firm* — Dorsey & Whitney LLP

(57) ABSTRACT

A soil analysis device is configured to create a soil sample solution. The device includes a reservoir configured to store an extractant, a mixing chamber coupled to the reservoir and configured to receive extractant from the reservoir and to receive a raw soil sample, and a control system. The control system is configured to determine an amount of extractant needed to produce, from the raw soil sample, a soil sample solution with a particular soil-to-extractant ratio and configured to cause the determined amount of extractant to be transferred from the reservoir to the mixing chamber.

19 Claims, 9 Drawing Sheets

Related U.S. Application Data continuation of application No. 13/797,546, filed on Mar. 12, 2013, now Pat. No. 9,291,545.

(60) Provisional application No. 61/697,718, filed on Sep. 6, 2012.

(51) Int. Cl.

| | |
|---|---|
| *G01N 15/06* | (2006.01) |
| *G01N 21/25* | (2006.01) |
| G01N 33/24 | (2006.01) |
| E02D 1/04 | (2006.01) |
| G01N 1/40 | (2006.01) |

(52) U.S. Cl.
CPC .............. *G01N 33/24* (2013.01); *E02D 1/04* (2013.01); *G01N 2001/383* (2013.01); *G01N 2001/4061* (2013.01); *G01N 2033/245* (2013.01)

(56) References Cited

U.S. PATENT DOCUMENTS

| | | | |
|---|---|---|---|
| 3,573,470 | A | 4/1971 | Haley |
| 3,861,802 | A | 1/1975 | Belmear, Jr. |
| 4,266,878 | A | 5/1981 | Auer |
| 4,997,281 | A | 3/1991 | Stark |
| 5,067,616 | A | 11/1991 | Plester et al. |
| 5,155,545 | A | 10/1992 | Rinke |
| 5,223,715 | A | 6/1993 | Taylor |
| 5,247,177 | A | 9/1993 | Goldberg et al. |
| 5,526,705 | A | 6/1996 | Skotnikov et al. |
| 5,887,491 | A | 3/1999 | Monson et al. |
| 5,974,889 | A | 11/1999 | Hanks |
| 6,287,358 | B1 | 9/2001 | Mason et al. |
| 6,324,922 | B1 | 12/2001 | Hanks |
| 6,356,830 | B1 | 3/2002 | Adamchuck et al. |
| 6,596,996 | B1 | 7/2003 | Stone et al. |
| 6,721,582 | B2 | 4/2004 | Trepagnier et al. |
| 6,831,746 | B2 | 12/2004 | Cassidy et al. |
| 6,931,950 | B2 | 8/2005 | Malachowski et al. |
| 6,937,939 | B1 | 8/2005 | Shibusawa et al. |
| 7,135,871 | B1 | 11/2006 | Pelletier |
| 7,188,450 | B2 | 3/2007 | Raun et al. |
| 7,216,555 | B2 | 5/2007 | Drummond et al. |
| 7,556,773 | B2 | 7/2009 | Horan et al. |
| 8,144,319 | B2 | 3/2012 | Preiner et al. |
| 8,446,586 | B2 | 5/2013 | Wu et al. |
| 8,472,023 | B2 | 6/2013 | Preiner et al. |
| 8,477,295 | B2 | 7/2013 | Preiner et al. |
| 9,291,545 | B1 | 3/2016 | White et al. |
| 2003/0025909 | A1 | 2/2003 | Hallstadius |
| 2003/0063276 | A1 | 4/2003 | Sjodin |
| 2003/0097947 | A1 | 5/2003 | Caruthers et al. |
| 2004/0009610 | A1 | 1/2004 | Schabron et al. |
| 2005/0042623 | A1 | 2/2005 | Ault-Riche et al. |
| 2006/0090219 | A1 | 4/2006 | Kisaka et al. |
| 2007/0013908 | A1 | 1/2007 | Lee et al. |
| 2007/0073491 | A1 | 3/2007 | Jahn et al. |
| 2007/0138401 | A1 | 6/2007 | Tokhtuev et al. |
| 2007/0141232 | A1 | 6/2007 | Tochterman |
| 2007/0228269 | A1 | 10/2007 | Miller et al. |
| 2008/0050762 | A1 | 2/2008 | Corey et al. |
| 2008/0128609 | A1 | 6/2008 | Miller et al. |
| 2008/0194033 | A1 | 8/2008 | Golitz |
| 2008/0198381 | A1 | 8/2008 | Heggs et al. |
| 2009/0166520 | A1 | 7/2009 | Tuli et al. |
| 2010/0003760 | A1 | 1/2010 | Agrawal et al. |
| 2010/0283993 | A1 | 11/2010 | Preiner et al. |
| 2011/0054864 | A1 | 3/2011 | Lundstedt et al. |
| 2011/0125477 | A1 | 5/2011 | Lightner et al. |
| 2012/0047988 | A1 | 3/2012 | Mehus |
| 2016/0247009 | A1 | 9/2016 | White |

OTHER PUBLICATIONS

U.S. Appl. No. 13/797,546, filed Mar. 12, 2013, Office Action, dated Aug. 7, 2015.

U.S. Appl. No. 13/797,546, filed Mar. 12, 2013, Restriction Requirement, dated Jul. 16, 2015.

U.S. Appl. No. 15/075,649, filed Mar. 21, 2016, Notice of Allowance, dated Apr. 25, 2017.

U.S. Appl. No. 15/075,649, dated Mar. 21, 2016, Office Action, dated Feb. 1, 2017.

Adamchuk, V.I. et al., "On-the-Go Mapping of Soil Properties Using Ion-Selective Electrodes", in: Stafford, J.V., Werner, A. (Ed.), Precision Agriculture, dated 2003, pp. 27-33.

Weishaar, J.L. et al., "Evaluation of Specific Ultraviolet Absorbance as an Indicator of the Chemical Composition and Reactivity of Dissolved Organic Carbon", Environmental Science and Technology, dated 2003, pp. 4702-4708, vol. 37, No. 20.

"World Greenhouse Gas Emissions by Sector", UNEP/GRID-Arendal, dated 2008, Online, from the internet http://maps.grida.no/go/graphic/world-green-house-gas-emis-sions-by-sector>.

Yao, H et al., "Hyperspectral Image Feature Extraction and Classification for Soil Nutrient Mapping", Precision Agriculture, Papers from the 4th European Conference on Precision Agriculture, Berlin, Germany, dated Jun. 15-19, 2003, p. 216.

"2007", Census of Agriculture Report, Issued Feb. 2009, pp. 1-739, Online, http://www.agcensus.usda.gov/>.

Bouvier, J.C. et al., "On-Line Monitoring of Nitrate and Nitrite by UV Spectropotometry in a SBR Process Used for the Treatment of Industrial Wastewaters", International Journal of Chemical Reactor Engineering, dated 2008, 21 pages, vol. 6.

Bravo, M. et al, "Nitrate Determination in Chilean Caliche Samples by UV-Visible Absorbance Measurements and Multivariate Calibration", J, Chil. Chem. Soc. Dated 2009, pp. 93-98, vol. 54, No. 1.

Crumpton, W.G., et al., "Nitrate and Organic N. Analyses with Second-Derivative Spectroscopy", Limnol., Oceanogr., dated 1992, pp. 907-913, vol. 37, No. 4.

"Dramatic Increases in Corn and Soybean Costs in 2009", Farm Economics: Facts and Opinions, dated Jul. 11, 2008, 4 pages. Online, http://www.farmdoc.illinois.edu/manage/newsletters/fefo08_13/fefo08_13.html>.

Dress, P. et al., "Water-Core Waveguide for Pollution Measurements in the Deep Ultraviolet", Applied Optics, dated Jul. 20, 1998, pp. 4991-4997, vol. 37, No. 21.

"EPP2000-HR High Resolution Miniature Spectrometers", dated 2010, StellarNet, Inc. 2 pages, Online, www.stellarnet-inc.com/products_spectrometers_EPP2000HR.htm>.

Ferree, M.A. "Evaluation of a Second Derivative UV/Visible Spectroscopy Technique for Nitrate and Total Nitrogen Analysis of Wastewater Samples", Wat. Res., dated 2001, pp. 327-332 vol. 32., No. 1.

"Grand Challenges for Engineering", National Academy of Engineering of the Natural Sciences, 2009, Online from Dec. 1, 2010, http://www.engineeringchallenges.org>.

Jahn, B.R. et al., "Mind-infrared Spectroscopic Determination of Soil Nitrate Content", Biosystems Engineering, dated 2006, pp. 505-515, vol. 94, No. 4.

Jannasch, H.W. et al., "The Land/Ocean Biogeochemical Observatory: A Robust Networked Mooring System for Continuously Monitoring Complex Biogeochemical Cycles in Estuaries", Limnology and Oceanography: Methods, dated 2008, pp. 263-276, vol. 6.

Johnson, K.S. et al., "In Situ Ultraviolet Spectrophotometry for High Resolution and Long Term Monitoring of Nitrate, Bromide and Bisulfide in the Ocean", Deep-Sea Research Part 1, dated 2002, pp. 1291-1305, vol. 49.

Karlsson, M. et al., "Determination of Nitrate in Municipal Waste Water by UV Spectroscopy", Analytica Chimica Acta, dated 1995, pp. 107-113, vol. 312.

Kim, H.J. et al., "Evaluation of Nitrate and Potassium Ion-Selective Membranes for Soil Macronutrient Sensing", Transactions of the ASABE, dated 2006, pp. 597-606, vol. 49, No. 3.

Lambert, D. et al., "Precision Agriculture Profitability Review", dated Sep. 15, 2000, pp. 1-154, Online dated Nov. 30, 2010, www.agriculture.purdue.edu/ssmc/>.

(56) References Cited

OTHER PUBLICATIONS

"Maya2000 Pro Delivers Serious Performance", 1989-2010, Ocean Optics, Inc. 2 pages. Retrieved online Nov. 30, 2010, Online www.oceanoptics.corn/products/maya.asp>.
PCT International Search Report and Written Opinion, PCT Application No. PCT/US2010/034048, dated Jul. 1, 2010, 8 pages.
PCT International Search Report and Written Opinion, PCT Application No. PCT/US2010/034053 dated Jul. 1, 2010, 9 pages.
Price, R.R. et al., "Rapid Nitrate Analysis of Soil Cores Using ISFETs", Transactions of the ASAE, dated 2003, pp. 1-10, vol. 46, No. 3.
Pruitt, P. "Nitrate Measurement in Less Than 30 Seconds", Water Environment Laboratory Solutions, dated Feb./Mar. 2009, pp. 1-15, vol. 16, No. 1.
Randall; G.W. et al., "Nitrate Nitrogen in Surface Waters as Influenced by Climatic Conditions and Agricultural Practices" Journal of Environmental Quality, dated 2001, pp. 337-344, vol. 30.
Ratako, A. et al., "Micro and Mini-Nitrate Sensors for Monitoring Soils, Ground water and Aquatic Systems", Center for Embedded Network Sensing, dated May 12, 2009, 3 pages.
Selk, G.E. et al., "Comparing the Accuracy of the Cardy Portable Nitrate Meter with Laboratory Analysis of Nitrate Concentrations in Summer Annual Forages", dated 2004, 4 pages. Online at http://www.ansiokstate.edu/research/2004rr/02/0-2htm>.
Sempere, A. et al,, "Simple Determination of Nitrate in Soils by Second-Derivative Spectroscopy", Journal of Soil Science, dated 1993, pp. 633-639, vol. 44.
Sethuramasamyraja B. et al., "Agitated Soil Measurement Method for integrated On-the-Go Mapping of Soil pH, Potassium and Nitrate Contents", Computers and Electronics in Agriculture, dated 2008, pp. 212-225, vol. 60.
Sibley, K.J., et al.. "Field-Scale Validation of an Automated Soil Nitrate Extraction and Measurement System", Precision Agriculture, dated 2009, pp. 162-174, vol. 10.
"Soil Nitrate Test Kit Instructions", NECi:, The Nitrate Elimination Company, Inc., Lake Linden, MI, dated 2009, 2 pages. Online www.nitrate.com/sntkl00series.pdf>.
Stark, P.C., et al., "Pre-PCR DNA Quantitation of Soil and Sediment Samples: Method Development and Instrument Design", Soil Biology and Biochemistry, 2000, pp. 1101-1110. vol. 32.
Thomas, O., et al., "Ultraviolet Multiwavelength Absorptiometry (UVMA) for the Examination of Natural Waters and Wastewaters, Part 1: General Considerations", Fresenius Journal of Analytical Chemistry, dated 1990, pp. 234-237, vol. 338.
Thomas, O., et al., "Ultraviolet Multiwavelength Absorptiometry (UVMA) for the Examination of Natural Waters and Wastewaters, Part II: General Considerations", Fresenius Journal of Analytical Chemistry, dated 1990, pp. 238-240, vol. 338.
Tuli, A. et al., "In situ Monitoring of Soil Solution Nitrate: Proof of Concept", Soil Science Society of America Journal, Mar.-Apr. 2009, pp. 501-509, vol. 73, No. 2.

SELF-FILLING SOIL PROCESSING CHAMBER WITH DYNAMIC EXTRACTANT VOLUME

BENEFIT CLAIM

This application claims the benefit under 35 U.S.C. § 120 as a Continuation of application Ser. No. 15/075,649, filed Mar. 21, 2016, issued as U.S. Pat. No. 9,739,693, which is a continuation of application Ser. No. 13/797,546, filed Mar. 12, 2013, issued as U.S. Pat. No. 9,291,545, which claims the benefit under 35 U.S.C. 119(e) of provisional application 61/697,718, filed Sept. 6, 2012, the entire contents of which are hereby incorporated by reference for all purposes as if fully set forth herein. The applicants hereby rescind any disclaimer of claim scope in the parent applications or the prosecution history thereof and advise the USPTO that the claims in this application may be broader than any claim in the parent applications.

BACKGROUND

1. Field of Art

The invention generally relates to the field of soil measurement and testing and in particular to automated measurement and testing of soil properties.

2. Background Information

Traditionally, a raw soil sample is processed by first completely drying it and then thoroughly grinding it so that it has a uniform moisture content and can be easily sub-sampled. This enables a soil sample to be efficiently processed at a low cost. However, the process of drying and grinding a soil sample can drastically change the resulting soil nutrient measurements. In particular, potassium levels can vary substantially with soil type and extent of drying performed before processing the sample.

More agronomically representative results can be achieved by performing field-moist analysis, instead of using a drying and grinding process. In one embodiment, a soil sample solution is prepared by combining a raw soil sample and an extractant (e.g., deionized water). Field-moist analysis is then performed on the solution. In order to increase the accuracy of the analysis, it is helpful to clean the equipment between soil samples.

SUMMARY

The above and other problems are addressed by a soil analysis device. One embodiment of the device is configured to create a soil sample solution and includes a reservoir configured to store an extractant, a mixing chamber coupled to the reservoir and configured to receive extractant from the reservoir and to receive a raw soil sample, and a control system. The control system is configured to determine an amount of extractant needed to produce, from the raw soil sample, a soil sample solution with a particular soil-to-extractant ratio and configured to cause the determined amount of extractant to be transferred from the reservoir to the mixing chamber.

Another embodiment of the device includes a reservoir configured to store a cleaning fluid, a mixing chamber coupled to the reservoir, and a control system. The mixing chamber is configured to produce a soil sample solution, output the produced soil sample solution, receive cleaning fluid from the reservoir, move the received cleaning fluid within the mixing chamber, and output the received cleaning fluid. The control system is configured to cause the cleaning fluid to be transferred from the reservoir to the mixing chamber, cause the mixing chamber to move the transferred cleaning fluid within the mixing chamber to rinse the mixing chamber, and cause the mixing chamber to output the transferred cleaning fluid.

DETAILED DESCRIPTION

The Figures (FIGS.) and the following description describe certain embodiments by way of illustration only. One skilled in the art will readily recognize from the following description that alternative embodiments of the structures and methods illustrated herein may be employed without departing from the principles described herein. Reference will now be made to several embodiments, examples of which are illustrated in the accompanying figures. It is noted that wherever practicable similar or like reference numbers may be used in the figures and may indicate similar or like functionality.

Structure of Soil Analysis Device

Figure 1:
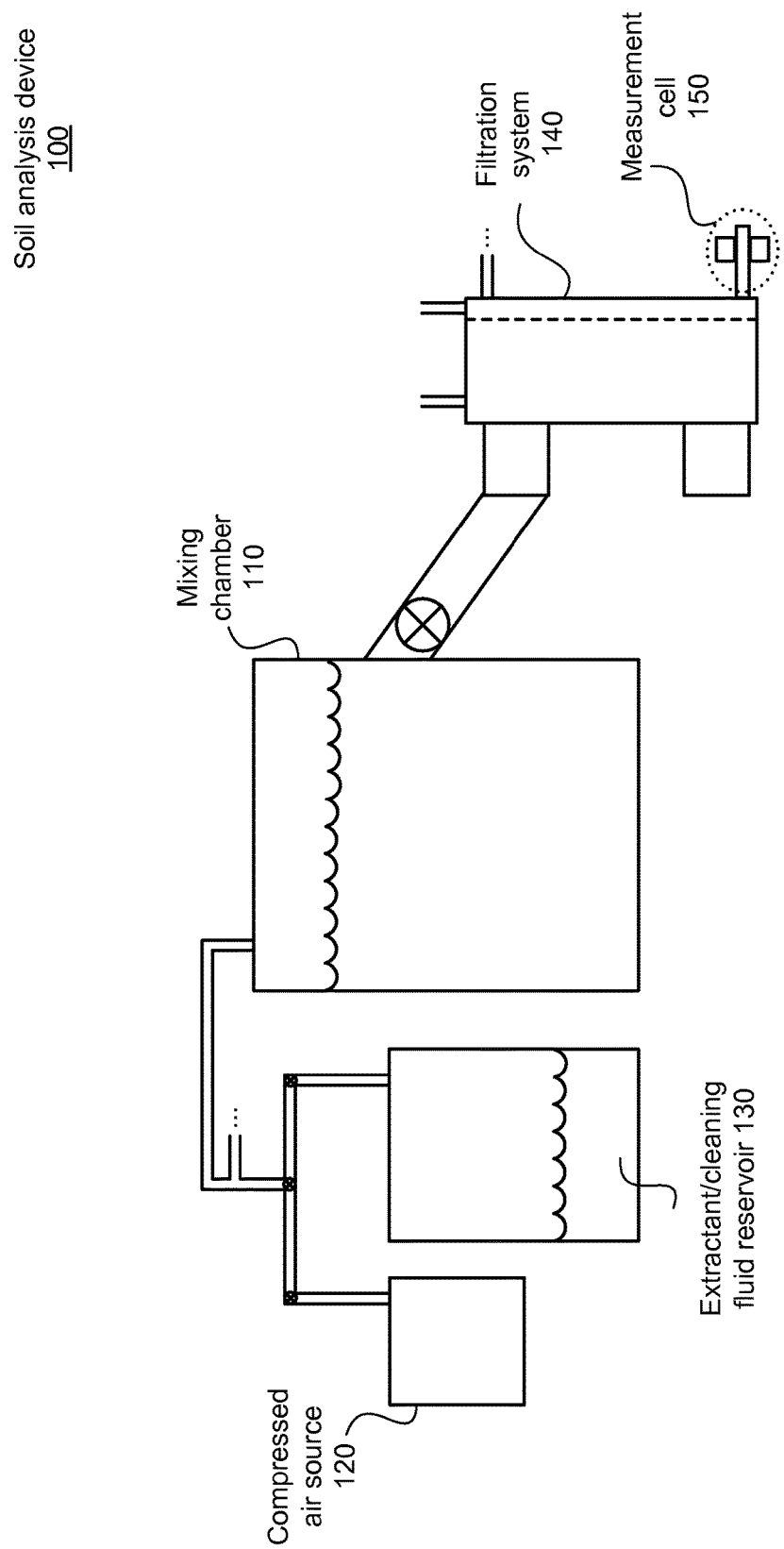
FIG. 1 is a block diagram of a soil analysis device configured to create a soil sample solution, according to one embodiment.

FIG. 1 is a block diagram of one embodiment of a soil analysis device 100. In one embodiment, the soil analysis device 100 includes a mixing chamber 110, a compressed air source 120, one or more reservoirs that contain extractant and/or cleaning fluid 130, a filtration system 140 and a measurement cell 150. In an alternative embodiment, the measurement cell 150 is absent and the device 100 comprises an output port (not shown) for apportioning out a volume of filtered solution for collection and testing external to the device 100. The soil analysis device 100 also includes a control system (not shown) for controlling the operation of the soil analysis device. The control system is described below with reference to FIGS. 6 and 7.

Generally, the mixing chamber 110 is configured to receive a raw soil sample and an extractant (e.g., deionized water), mix them together, and provide the mixed solution (or "slurry") to the filtration system 140. The filtration system 140 filters the slurry and provides the filtered output to the measurement cell 150 for testing, or the filtration system dispenses the raw slurry through an output port (without filtering it) for further processing and analysis. In one embodiment, the control system causes extractant to be moved from a reservoir 130 to the mixing chamber 110. In another embodiment, the control system causes the soil analysis device 100 to use air from the compressed air source 120 and a cleaning fluid (e.g., deionized water) from a reservoir 130 to automate self-cleaning of the mixing chamber 110, filtration system 140, and/or the measurement cell 150 or output port. Cleaning the various components of the device 100 ensures that the analysis of a later-received soil sample is not tainted by a previously-received soil sample.

Figure 2:
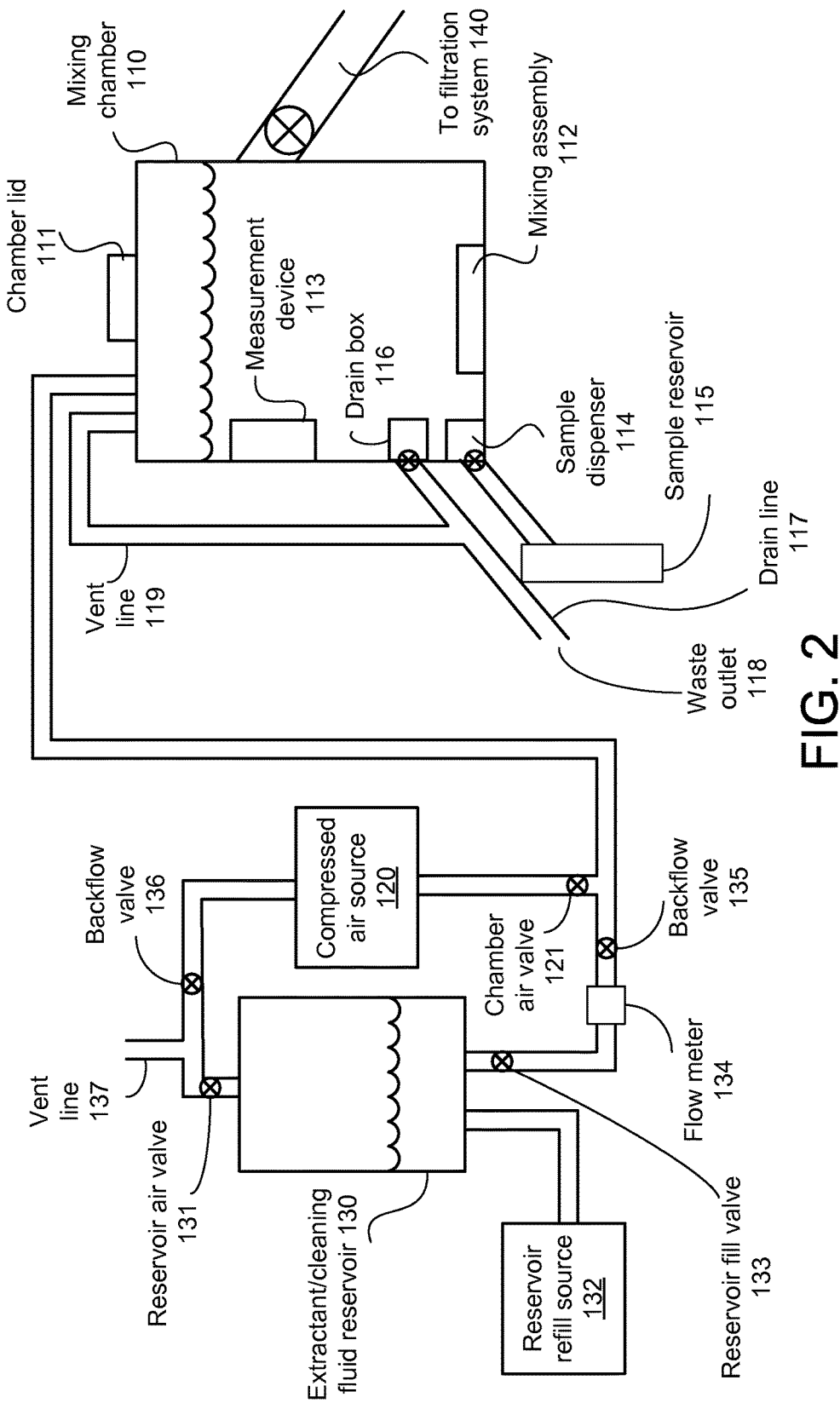
FIG. 2 is a block diagram providing more detail regarding the mixing chamber, compressed air source, and reservoir shown in FIG. 1, according to one embodiment.

FIG. 2 is a block diagram providing more detail regarding the mixing chamber 110, compressed air source 120, and reservoir 130 shown in FIG. 1, according to one embodiment. Like FIG. 1, FIG. 2 shows a mixing chamber 110, a compressed air source 120, and a reservoir that contains extractant and/or cleaning fluid 130. The mixing chamber 110 is coupled to the reservoir 130 using one or more pipes and/or tubes. The mixing chamber 110 is also coupled to the compressed air source 120 using one or more pipes and/or tubes. The reservoir 130 is also coupled to the compressed air source 120 using one or more pipes and/or tubes.

Unlike FIG. 1, FIG. 2 also shows additional elements related to the mixing chamber 110, the compressed air source 120, and the reservoir 130. In the embodiment illustrated in FIG. 2, the mixing chamber 110 includes a chamber lid 111, a mixing assembly 112, a measurement device 113, a sample dispenser 114, and a drain box 116. The mixing chamber 110 includes an entry port (not shown) that can be used to add material to and/or remove material from the mixing chamber. For example, the entry port can be used to add a raw soil sample to the mixing chamber. Material can be added to or removed from the mixing chamber manually or through an automated mechanism. The chamber lid 111 seals this entry port and can be moved if desired (e.g., to gain access to the entry port). In one embodiment, the chamber lid 111 includes an actuator that can be controlled to move the lid. For purposes of illustration, FIG. 2 depicts an embodiment where the chamber lid 111 (and, therefore, the entry port) is located at the top of the mixing chamber 110. However, the chamber lid 111 (and, therefore, the entry port) can be located elsewhere (e.g., on the side of the mixing chamber 110).

The mixing assembly 112 mixes the contents of the mixing chamber 110 (e.g., a raw soil sample and extractant) to produce a homogenized soil sample solution. The mixing assembly 112 can use any suitable mixing method. In one embodiment, the mixing assembly 112 includes one or more blades attached to a motor. The motion of the motor causes the blades to spin, thereby mixing the contents of the mixing chamber 110. The operation of the motor and the movement of the blades produce a soil sample solution by agitating the contents of the mixing chamber 110. In one embodiment, the motor and blades agitate the contents for a predetermined length of time or until receiving a control signal from an external controller. For purposes of illustration, FIG. 2 depicts an embodiment where the mixing assembly 112 is located at the bottom of the mixing chamber 110. However, the mixing assembly 112 can be configured to operate anywhere within the mixing chamber 110.

In one embodiment, the motor is connected to a mixing shaft to facilitate mixing the contents of the mixing chamber 110. In one embodiment, the mixing shaft enters the mixing chamber 110 from an entry port on the top of the mixing chamber 110. In other embodiments, however, the mixing shaft enters the mixing chamber 110 from an opening on the bottom or side of the mixing chamber 110.

In other embodiments, the mixing assembly 112 can use one or more of sonication, heating or chemical addition, or any other method of mixing or combination of methods of mixing to combine the contents of the mixing chamber 110. In one embodiment, ultrasonic waves from a source are applied to the contents to reduce the amount of particulates by breaking up soil. In another embodiment, a centrifugal force is applied to the contents to separate particulates from fluid material. The separated particulates can then be removed from the mixing chamber 110.

In one embodiment, the mixing assembly 112 includes a turbulence-inducing feature that facilitates the mixing of the contents of the mixing chamber 110. In one embodiment, the turbulence-inducing feature is a flat bar introducing into a cylindrical mixing chamber 110. The operation of the motor with attached blades or mixing shaft can create an approximately circular flow that circulates the contents of the mixing chamber 110 without effectively mixing the contents. The addition of a flat bar interrupts the regularized motion (or flow) of the contents of the mixing chamber 110 while the motor is in operation, creating a more turbulent flow that improves the mixing of the contents of the mixing chamber 110. Thus, the addition of the turbulence-inducing feature decreases the amount of time needed to mix the contents of the mixing chamber 110 to create the soil sample solution.

The measurement device 113 is discussed below.

In the embodiment illustrated in FIG. 2, the mixing chamber 110 includes three outlet ports, which enable removal of the contents of the mixing chamber 110. In one embodiment, an outlet port is an opening having a valve and/or a movable cover, so that opening the valve and/or moving the cover enables drainage of the contents of the mixing chamber 110. One port leads to the filtration system 140, one port (the sample dispenser 114) leads to a sample reservoir 115, and one port (the drain box 116) leads to a waste outlet 118. The sample dispenser 114 drains the contents of the mixing chamber 110 into a sample reservoir 115. The contents of the sample reservoir 115 can then be removed and either stored for future use or further processed for measurement by a separate system such as an inductively-coupled-plasma atomic-emission-spectoscopy (ICP-AES) tool, flow-injection-analyzer (FIA) tool, or ion selective electrode (ISE) tool. The drain box 116 drains the contents of the mixing chamber 110 through a drain line 117 to a waste outlet 118 for disposal. The mixing chamber 110 also includes a vent line 119, which enables the contents of the mixing chamber 110 to overflow into the drain line 117.

The reservoir that contains extractant and/or cleaning fluid 130 is configured to provide that extractant and/or cleaning fluid to the mixing chamber 110 through one or more pipes and/or tubes. In one embodiment, the mixing chamber 110 receives a raw soil sample through its entry port but receives extractant and/or cleaning fluid from the reservoir 130 through the one or more pipes and/or tubes.

The reservoir 130 stores extractant and/or cleaning fluid in a pressurized manner using compressed air source 120, reservoir air valve 131, and reservoir fill valve 133. The reservoir air valve 131 is located between the compressed air source 120 and the reservoir 130 within a pipe or tube coupling the compressed air source 120 to the reservoir 130. The reservoir fill valve 133 is located between the reservoir 130 and the mixing chamber 110 within a pipe or tube coupling the reservoir 130 to the mixing chamber 110.

In one embodiment, extractant and/or cleaning fluid is moved from the reservoir 130 to the mixing chamber 110 as follows: The reservoir air valve 131 and the reservoir fill valve 133 open. The chamber air valve 121 closes. The compressed air source 120 pushes air through the backflow valve 136 and the reservoir air valve 131 into the pressurized reservoir 130. The backflow valve 136 prevents fluid from flowing from the pressurized reservoir 130 to the compressed air source 120. The vent line 137 allows air to flow out of the reservoir 130 during filling. The air entering the pressurized reservoir 130 causes extractant and/or cleaning fluid to exit the reservoir 130 through the reservoir fill valve 133. The exiting extractant and/or cleaning fluid flows through a flow meter 134, which measures the flow of the extractant and/or cleaning fluid. The amount of the measured flow is used to determine how much extractant and/or cleaning fluid is being added to the mixing chamber 110 (further explained below). After flowing through the flow meter 134, the extractant and/or cleaning fluid flows through the backflow valve 135 and eventually enters the mixing chamber 110. The backflow valve 135 prevents fluid from flowing from the mixing chamber 110 to the reservoir 130. In one embodiment, a spray nozzle (not shown) is used to add the extractant and/or cleaning fluid to the mixing chamber 110.

The reservoir 130 acts as a separate container for collecting and storing extractants, so that when a soil measurement is to be performed, extractant is ready for use and can be transferred to the mixing chamber 110. For example, the reservoir 130 can store a large volume of extractant (e.g., one liter or more) and can transfer this extractant to the mixing chamber 110 in a short amount of time (e.g., a few seconds). This is particularly useful if it is time-consuming to generate large amounts of the extractant. For example, the process for generating large volumes of deionized water (one example of an extractant) requires time on the order of minutes per liter.

In one embodiment, the reservoir 130 is refilled while a soil sample measurement is taking place, thereby decreasing the amount of time required to prepare the soil analysis device 100 for the next soil sample to be analyzed. In one embodiment, the reservoir 130 is coupled to a reservoir refill source 132 by one or more pipes and/or tubes. The reservoir 130 is refilled by transferring extractant and/or cleaning fluid from the reservoir refill source 132 to the reservoir 130 through the one or more pipes and/or tubes.

It is sometimes desirable to add a particular amount of extractant and/or cleaning fluid to the mixing chamber 110. For example, a particular amount of extractant is needed in order to prepare a soil sample solution with a particular soil-to-extractant ratio. In this situation, it is necessary to determine how much extractant and/or cleaning fluid has been added to the mixing chamber 110 so far and whether additional extractant and/or cleaning fluid is needed. Recall that the flow meter 134 measures the flow of the extractant and/or cleaning fluid out of the reservoir 130 on its way to the mixing chamber 130. However, the amount of the measured flow is not necessarily the only extractant and/or cleaning fluid that is being added to the mixing chamber. Additional extractant and/or cleaning fluid might already be present in the pipes and/or tubes between the flow meter 134 and the mixing chamber 110. This additional amount (of unknown size) would also be added to the mixing chamber, making it difficult to determine the exact amount of extractant and/or cleaning fluid that is being added.

To address this problem, the compressed air source 120 can be used to clear out pipes and/or tubes (leading to the mixing chamber 110) of their contents. Once the relevant pipes and/or tubes have been cleared out, the flow meter 134 can be used to indicate exactly how much extractant and/or cleaning fluid is being added to the mixing chamber. In one embodiment, these pipes and/or tubes are cleared of their contents as follows: The chamber air valve 121 opens. The compressed air source 120 pushes air through the chamber air valve 121. After flowing through the chamber air valve 121, the air flows through the relevant pipes and/or tubes, clearing them of their contents. (The backflow valve 135 prevents the air from flowing to the reservoir 130.) Eventually, the air (and the former contents of the pipes and/or tubes) enters the mixing chamber 110. The mixing chamber 110 can then be emptied and cleaned, as described below.

Recall that the soil analysis device 100 performs field-moist analysis on a soil sample solution. In order to increase the accuracy of the analysis, it is helpful to clean the equipment (e.g., the mixing chamber 110, filtration system 140, and/or measurement cell 150) between soil samples. To make this process easier, the soil analysis device 100 can be configured to self-clean between soil samples. Once the soil analysis device has been cleaned, the next soil sample can be loaded and analyzed.

In one embodiment, the soil analysis device 100 cleans itself as follows: The drain box 116 opens, thereby releasing the contents of the mixing chamber 110 (e.g., the remains of a previous soil sample solution) into the drain line 117 and substantially emptying the mixing chamber 110. The drain box 116 then closes. Cleaning fluid (e.g., deionized water) is transferred from a reservoir 130 to the mixing chamber 110. In one embodiment, a spray nozzle (not shown) is used to add the cleaning fluid to the mixing chamber 110. Using a spray nozzle (e.g., a full-cone spray nozzle) helps spray clean the sidewalls of the mixing chamber 110. The mixing assembly 112 moves the cleaning fluid within the mixing chamber 100 to rinse the chamber. The drain box 116 opens, thereby releasing the contents of the mixing chamber 110 (e.g., cleaning fluid and leftover soil sample solution) into the drain line 117 and substantially emptying the mixing chamber 110. Pressurized air is transferred from the compressed air source 120 to the mixing chamber 110 (e.g., by activating the compressed air source 120 and opening the chamber air valve 121). The pressurized air pushes any remaining contents of the mixing chamber 110 (e.g., cleaning fluid and leftover soil sample solution) through the drain box 116 and into the drain line 117, thereby drying the mixing chamber 110. The drain box 116 then closes. The mixing chamber 110 is now ready to receive a new soil sample.

Figure 3:
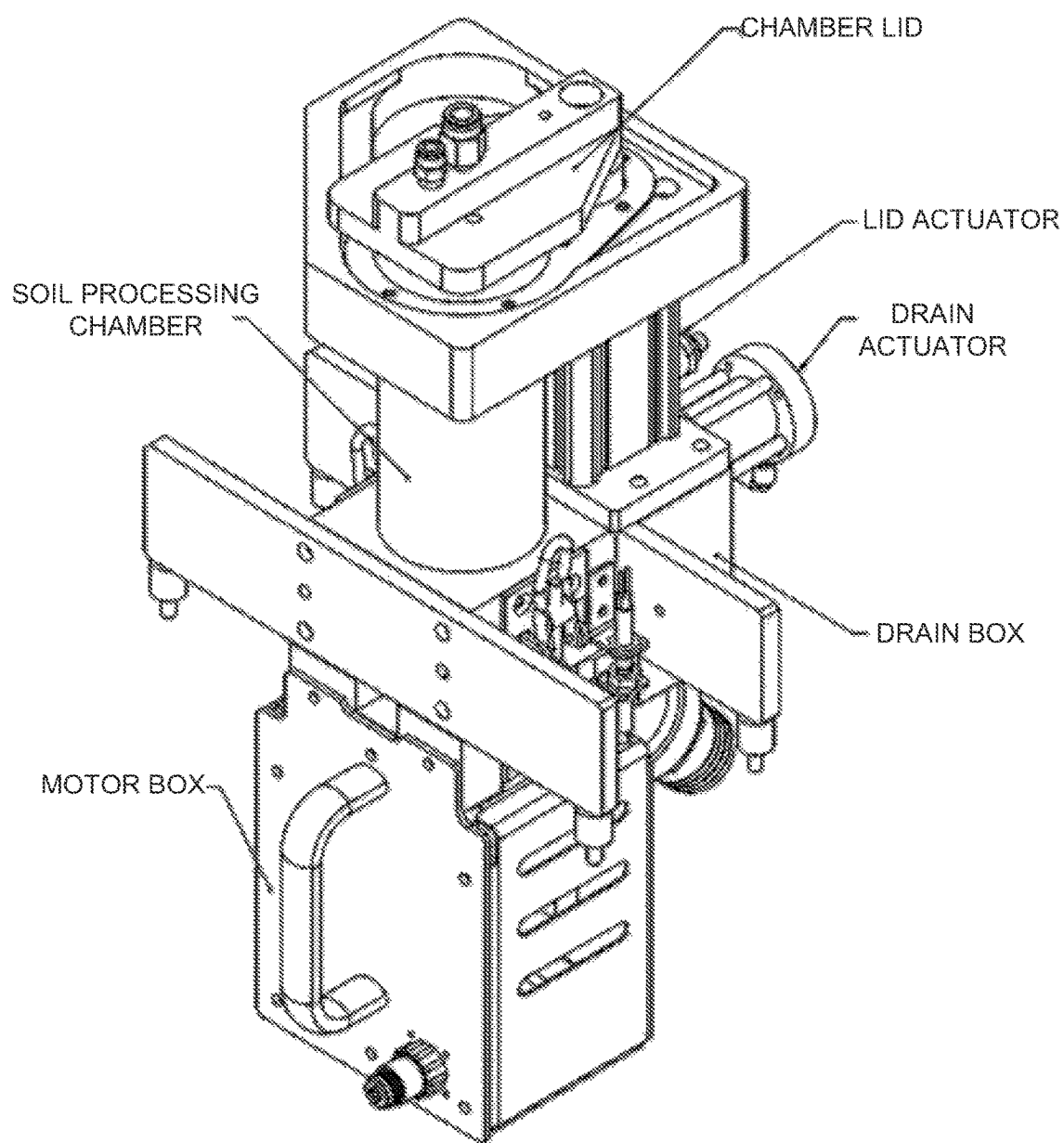
FIG. 3 is a three-dimensional external view of the mixing chamber shown in FIG. 1, according to one embodiment.

FIG. 3 is a three-dimensional external view of the mixing chamber 110 shown in FIG. 1, according to one embodiment. Various elements of FIG. 3 correspond to various elements of FIG. 2, as follows: "CHAMBER LID" corresponds to chamber lid 111. "SOIL PROCESSING CHAMBER" corresponds to mixing chamber 110. "DRAIN BOX" corresponds to drain box 116. "MOTOR BOX" corresponds to mixing assembly 112.

Figure 4:
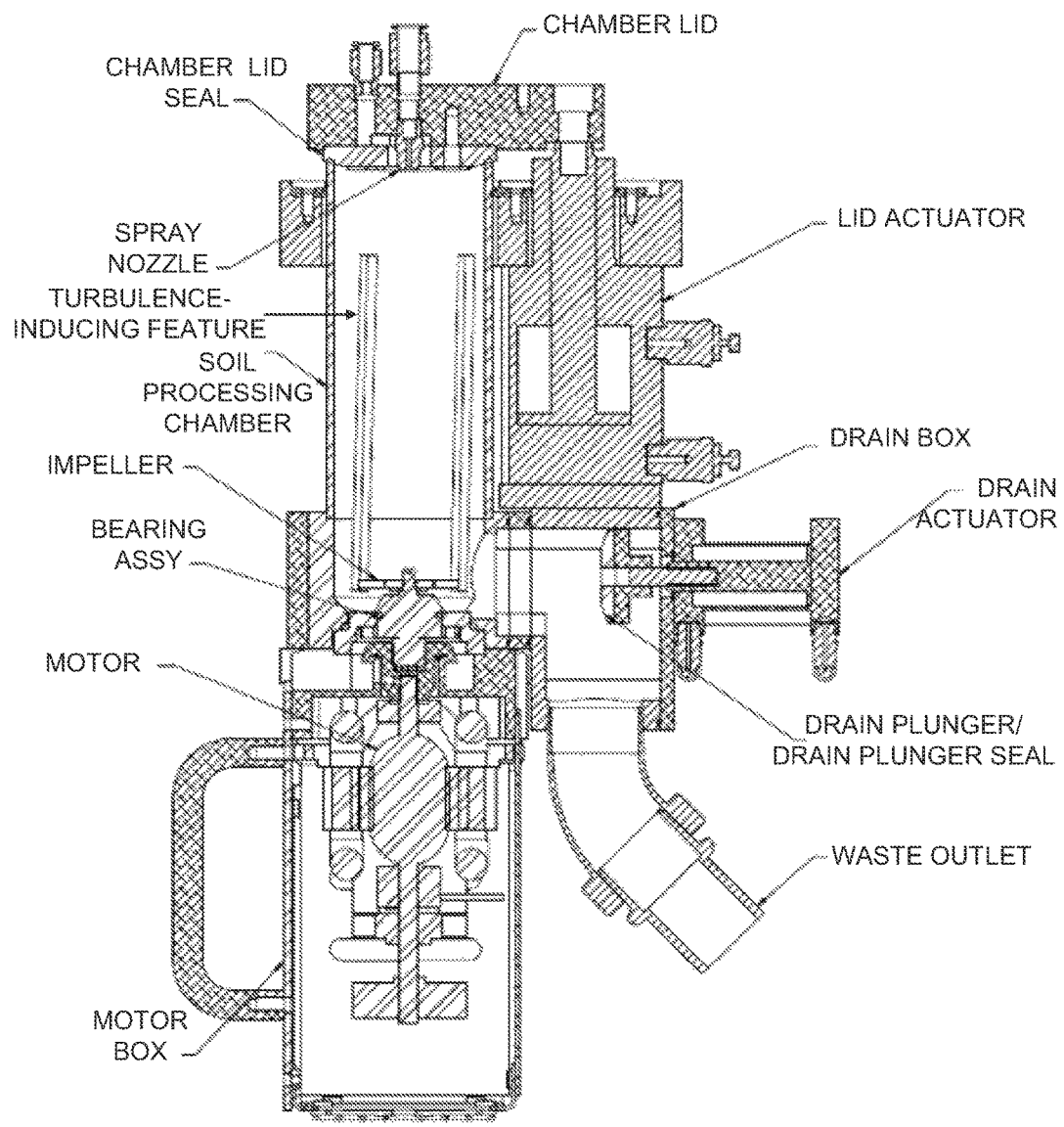
FIG. 4 is a cross-sectional view of the mixing chamber shown in FIG. 1, according to one embodiment.

FIG. 4 is a cross-sectional view of the mixing chamber 110 shown in FIG. 1, according to one embodiment. Various elements of FIG. 4 correspond to various elements of FIG. 2, as follows: "CHAMBER LID" corresponds to chamber lid 111. "SOIL PROCESSING CHAMBER" corresponds to mixing chamber 110. "DRAIN BOX" corresponds to drain box 116. "MOTOR BOX", "MOTOR", "IMPELLER", and "BEARING ASSEMBLY" correspond to mixing assembly 112. "WASTE OUTLET" corresponds to waste outlet 118.

Figure 5:
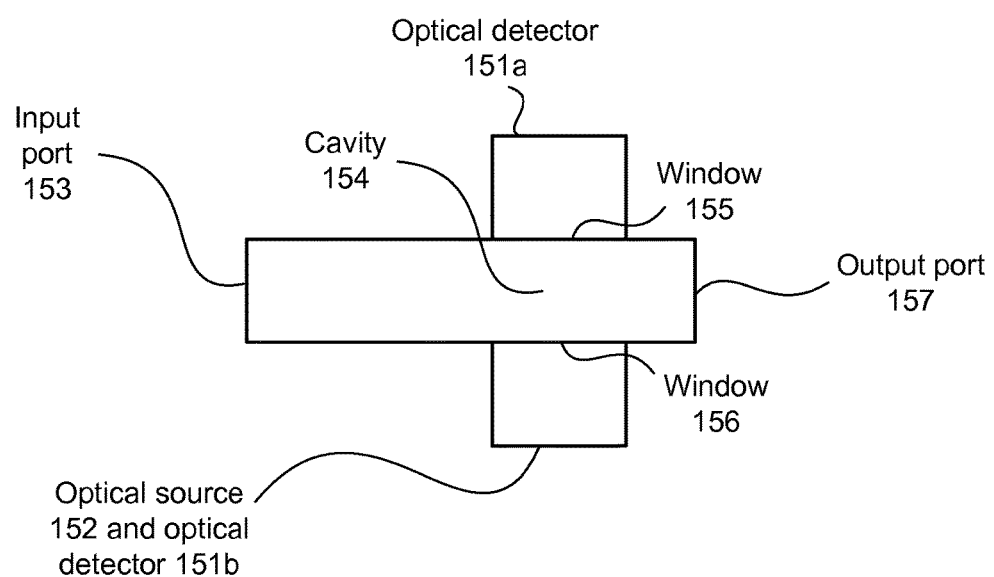
FIG. 5 is a block diagram of a measurement cell for analyzing a soil sample solution, according to one embodiment.

FIG. 5 is a block diagram of a measurement cell 150 for analyzing a soil sample solution, according to one embodiment. The measurement cell 150 is configured to optically measure characteristics of the soil sample solution received from the filtration system 140. The measurement cell 150 includes or is coupled to an input port 153 for receiving the soil sample solution, a cavity 154, one or more windows 155, 156, an optical source 152, one or more optical detectors 151a, 151b, and an output port 157.

The optical source 152 initiates the measurement of the characteristics of the soil sample solution by passing light through the soil sample solution. A detector 151a is placed opposite from the optical source 152 across the cavity 154, to capture an attenuation spectrum of the light passing through the soil sample solution as a function of wavelength. In one embodiment, detectors 151 are spectrometers having a 1 to 4 nanometer resolution. The detectors 151 have a sufficient sensitivity to allow detection of light passing through materials having a high absorbance. This allows the detectors 151 to determine an attenuation spectrum associated with a soil sample solution by determining how different wavelengths of light are attenuated by the soil sample solution present in the cavity 154.

In one embodiment, a second detector 151b is placed on the same side of the cavity 154 as the light source 152, in order to obtain a reflection spectrum of the light reflected from the soil sample solution. The reflection spectrum may be used to determine characteristics of the soil sample.

Peaks in the attenuation spectrum allow identification of components of the soil. For example, attenuation peaks at wavelengths of approximately 200 nanometers and 300 nanometers indicate nitrate-nitrogen in the soil. Similarly, attenuation peaks at wavelengths of approximately 210 nanometers, 230 nanometers and 250-300 nanometers may be used to identify nitrite-nitrogen, bisulfide and organic carbon, respectively, in the soil. Other peaks in the attenuation spectrum may also be used to identify additional components of the soil. Additionally, if the soil sample solution contains chemicals in addition to soil and extractant, additional attributes of the soil in a sample may be determined from the effect of the chemicals on the attenuation spectrum. For example, if the soil sample solution includes a pH indicator, data captured by the detector 151a may be used to monitor the pH indicator and ascertain soil pH. As another example, the soil sample solution may include acids and/or reagents to enable the detector 151a to measure the amount of phosphorous or potassium in the soil.

In one embodiment, the light source 152 comprises a dual ultraviolet-visible/near-infrared light bulb, such as a dual tungsten-deuterium bulb. The light source 152 allows independent control of the production of ultraviolet light, visible light and near-infrared light. For example, modification of a tungsten filament in the light source 152 modifies production of light having wavelengths of 320 nanometers or longer ("visible light" and "near-infrared light"), while modification of a deuterium filament in the light source 152 modifies production of light having wavelengths shorter than 400 nanometers ("ultraviolet light" or "UV light").

The light source 152 may include a light source holder (not shown) connected to the window 156, where the light source holder includes an opening enabling the coupling of light (either by an optical fiber or by free-space optics) to the window 156. For example, an optical fiber inserted into the opening in the light source holder directs light from the light source 152 through the optical fiber to the window 156.

Light emitted from the light source 152 travels an optical path length from the window 156 covering light source 152 to the window 155 covering detector 151a. The optical path length affects the amount of light captured by a detector 151. Thus, modifying the distance between window 156 and window 155 affects the amount of visible or ultraviolet light absorbed by the soil sample solution in the measurement cell. In one embodiment, the optical path length between windows 156 and 155 is one millimeter.

Windows 156 and 155 isolate the source 152 and detectors 151 from the soil sample solution present in the cavity 154. Windows 156 and 155 have a high transmission of infrared, ultraviolet and visible light. For example, windows 156 and 155 may include quartz or fused-silica windows. In one embodiment, the windows 156 and 155 include a hydrophilic film, such as a film of silicon dioxide, to reduce the likelihood of air bubbles developing near the windows. Alternatively the windows 156 and 155 are made from a hydrophilic material. In one embodiment, the windows 156 and 155 include a non-stick coating such as a TEFLON coating.

Filtration of the soil sample solution by the filtration system 140 slows down the rate at which soil sample solution arrives at the measurement cell 150 for measurement. In some cases, filtration may cause one drop at a time to pass through the filtration system 140 and enter cavity 154, which depending upon the cavity 154 may cause surface effects on windows 156 and 155. Surface effects include, for example, splashing or the formation of bubbles.

In one embodiment, cavity 154 is sloped in order to prevent the occurrence of surface effects on windows 156 and 155. The cavity 154 may, for example, be slanted (e.g., angled) or curved. The slope mitigates the kinetic energy of the soil sample solution that has been filtered by the filtration system 140, thereby inhibiting the creation of surface effects on windows 156 and 155. As a consequence, windows 156 and 155 are more likely to be uniformly covered by a soil sample solution. This improves the optical measurement of soil characteristics, by creating a more consistent optical path for light that is transmitted or reflected by the soil sample solution.

The measurement cell 150 additionally includes an output port 157 for clearing the contents of the measurement cell 150. The output port 157 may additionally be used to input cleaning fluid to provide backpressure to clean the measurement cell 150 and/or the filtration system 140. To perform cleaning, the output port 157 may be coupled to a standard solenoid valve that opens and closes to allow fluid and air to flow through.

In one embodiment, the soil analysis device 100 may include a number of measurement cells 150 allowing the measurement of different characteristics of the soil sample simultaneously. For example, a second measurement cell may be used to measure soil pH concurrently with the measurement of other soil nutrients.

In addition to measurements performed by the measurement cell 150, the soil analysis device 100 may also include additional measurement devices 113 in mixing chamber 110 for performing further measurements of the soil sample. Examples of measurement devices 113 include a conductivity probe, a glass pH electrode, and ion selective electrodes including membranes for measuring various nutrients such as nitrate and potassium. The additional measurement devices 113 may also determine a moisture content of a soil sample, a viscosity of the soil sample or the soil sample solution, the temperature of the soil sample or the soil sample solution, or any other suitable characteristics of the soil sample or the soil sample solution. The data determined by the additional measurement devices 113 may be combined with the attenuation spectrum determined by the detector 151 to increase the accuracy of nutrient identification in the soil sample. For example, determining the moisture content of the soil sample allows improvement of a nitrate-nitrogen measurement by subtracting the weight of moisture in the soil sample from the weight of the soil sample. In one embodiment, an additional measurement device 113 captures optical reflectivity measurements of the soil in the mixing chamber 110, before extractant mixing, in the UV, visible, near IR and/or mid IR spectra. The reflectivity of dry soil as a function of wavelength may be correlated to soil type. Such information can be used, in conjunction with the other embodiments discussed herein to provide data about soil characteristics or to refine the measurement of soil characteristics in the measurement cell 150.

The soil analysis device 100 allows for near real-time analysis of soil components by integrating mixing of a soil sample and extractant with analysis of the resulting soil sample solution. For example, the soil measurement of interest is often a final value after all relevant nutrients in the soil have been extracted from the soil sample solution, which may take a significant amount of time. By integrating a high-speed measurement (typically less than 1 second per measurement) measurement cell 150 and coupling it to the mixing chamber 110, the measurement can be performed by the measurement cell 150 many times as the nutrient is being extracted and as the soil sample solution filters through the filtration system 140, allowing the final value of the nutrient to be accurately extrapolated in a much shorter amount of time. In contrast, conventional techniques of soil measurement are time-intensive because they rely on discrete steps of pre-processing the soil, extracting nutrients and then measuring nutrients, preventing these conventional methods from obtaining multiple measurements of soil characteristics during the measurement process.

The flow through rate of the filtration system 140 may be slow enough that air bubbles may occasionally become trapped in between drops of soil sample solution arriving in the measurement cell 150 from the filtration system 140. The air bubbles cause the filtering soil sample solution to become backed up, and can alter measurements of the soil sample solution. To prevent this, in one embodiment the soil analysis includes an overflow line (not shown) before the cavity 154. The overflow line allows trapped air bubbles to escape, allowing filtered soil sample solution to take their place instead. The overflow line is positioned proximately to the filtration system 140 above, vertically, the measurement cell 150 to allow the air to escape.

The overflow line also provides a place where filtered soil sample solution may go once the measurement cell 150 has filled with filtered soil sample solution. The overflow line thus removes excess filtered soil sample solution that is not needed for measurement.

In an alternative embodiment, the shape of the measurement cell 150 may be modified into a "V" shape by adding an upward sloping overflow line at the bottom point of the cavity 154. In this embodiment, the overflow line slopes in a different direction than the input to cavity 154, forming the V-shape. The second portion of the V-shape is formed by the overflow line, allowing trapped air bubbles and excess filtered soil sample solution to escape from the measurement cell 150. In this embodiment, the other elements of the measurement cell 150 such as the light source 152, detector(s) 151, and windows 156 and 155 may be located out-of-plane from the V-shape. The output port 157 may be located at the bottom of the V-shape next to cavity 154.

Figure 6:
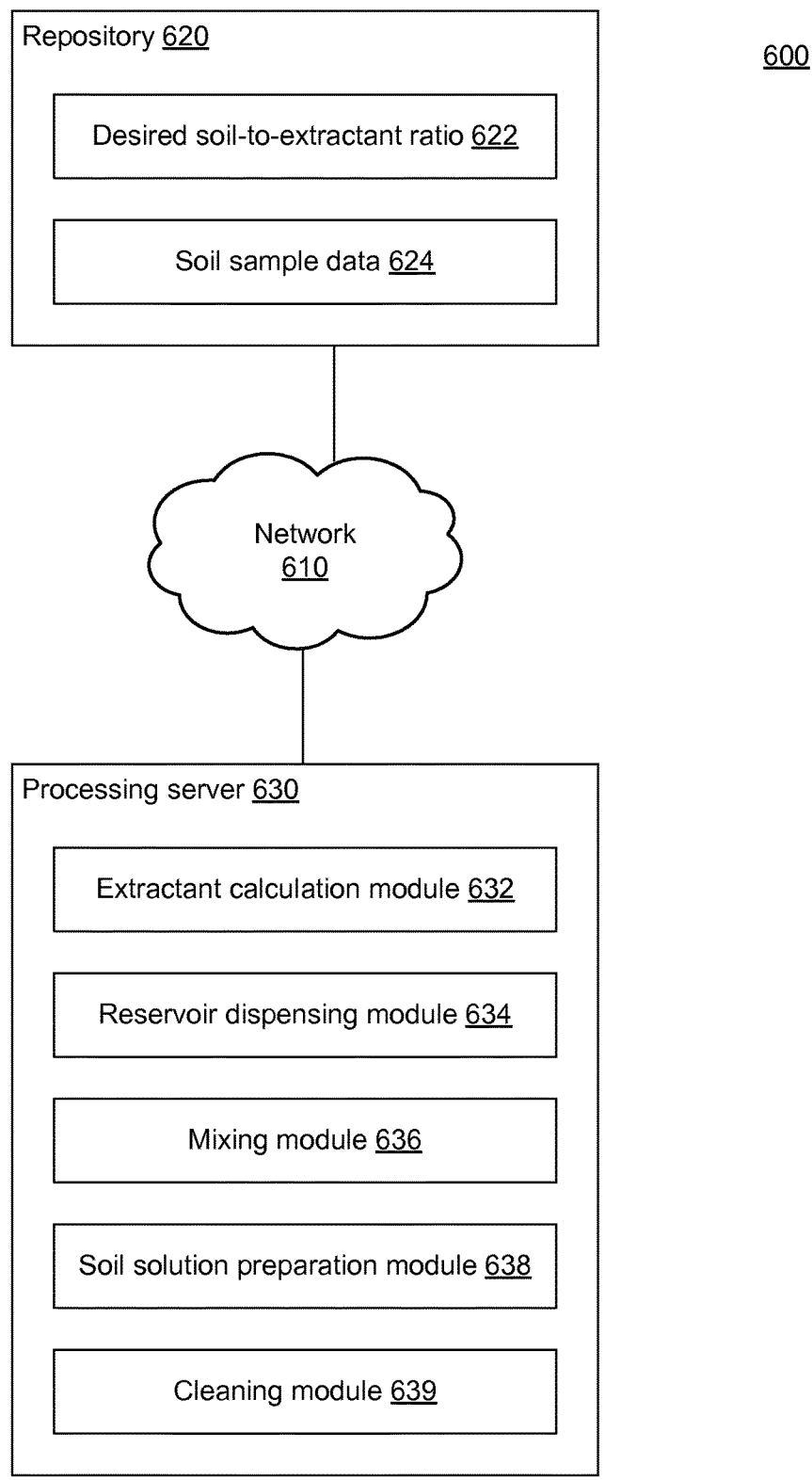
FIG. 6 is a high-level block diagram illustrating a system for controlling a soil analysis device configured to create a soil sample solution, according to one embodiment.

FIG. 6 is a high-level block diagram illustrating a system 600 for controlling a soil analysis device configured to create a soil sample solution, according to one embodiment. For example, the system 600 controls operation of the soil analysis device 100. As shown, the system 600 includes a network 610, a repository 620, and a processing server 630. The repository 620 stores data that can be used in controlling operation of the soil analysis device 100. The processing server 630 stores computer program modules (e.g., executable computer program instructions and/or other logic) that can be used in controlling operation of the soil analysis device 100. While only one of each entity is shown in the embodiment depicted in FIG. 6 for clarity, other embodiments can have multiple repositories 620 and/or processing servers 630.

The network 610 represents the communication pathway between the repository 620 and the processing server 630. In one embodiment, the network 610 uses standard communications technologies and/or protocols and can include the Internet. Thus, the network 610 can include links using technologies such as Ethernet, 802.11, worldwide interoperability for microwave access (WiMAX), 2G/3G/4G mobile communications protocols, digital subscriber line (DSL), asynchronous transfer mode (ATM), InfiniBand, PCI Express Advanced Switching, etc. Similarly, the networking protocols used on the network 610 can include multiprotocol label switching (MPLS), transmission control protocol/Internet protocol (TCP/IP), User Datagram Protocol (UDP), hypertext transport protocol (HTTP), simple mail transfer protocol (SMTP), file transfer protocol (FTP), etc. The data exchanged over the network 610 can be represented using technologies and/or formats including image data in binary form (e.g. Portable Network Graphics (PNG)), hypertext markup language (HTML), extensible markup language (XML), etc. In addition, all or some of the links can be encrypted using conventional encryption technologies such as secure sockets layer (SSL), transport layer security (TLS), virtual private networks (VPNs), Internet Protocol security (IPsec), etc. In another embodiment, the entities on the network 610 can use custom and/or dedicated data communications technologies instead of, or in addition to, the ones described above.

The repository 620 is a computer (or set of computers) that stores a desired soil-to-extractant ratio 622 and soil sample data 624. In one embodiment, the repository 620 includes a server that provides the processing server 630 read and write access to the desired soil-to-extractant ratio 622 and soil sample data 624 in response to requests.

The desired soil-to-extractant ratio 622 is a ratio representing the amount of soil versus moisture in a soil sample solution. Recall that a soil sample solution is prepared by combining a raw soil sample and an extractant (e.g., deionized water). Field-moist analysis is then performed on the solution. It is sometimes desirable to create a soil sample solution with a particular ratio of soil and moisture (e.g., 1:1, 1:2, 1:3, or 1:10). The soil-to-extractant ratio in this desired soil sample solution is stored as the desired soil-to-extractant ratio 622. In one embodiment, the desired soil-to-extractant ratio 622 contains a default value that can be overridden by a provided value (e.g., a value provided by a user or by a file). In another embodiment (not shown), the repository 620 stores multiple soil-to-extractant ratios (e.g., so that the ratios can be provided to a user to choose from), and one of these ratios is indicated (e.g., flagged) as the desired soil-to-extractant ratio 622.

Soil sample data 624 includes information regarding the mass and the moisture content of one or more raw soil samples. Each raw soil sample has a particular mass and a particular moisture content and is assigned a unique identifier. The soil sample data 624 associates this unique identifier with information regarding the mass and the moisture content of the identified raw soil sample. In one embodiment, the soil sample data 624 is stored in a database.

In one embodiment, the unique identifier is a single value assigned to only one sample. In another embodiment, the unique identifier is a pair of values, where one value indicates a particular batch of different samples and another value indicates the sample's position within that batch. The unique identifier can be partially or fully encoded in a machine-readable form such as a barcode or a radio frequency identifier (RFID) tag. This machine-readable form can then be affixed to the sample container.

Note that storing a soil sample's mass information and moisture information electronically as soil sample data 624 is optional. In a different embodiment, a soil sample's mass information and moisture information are affixed to the sample's container (e.g., by manually writing the information on the container) instead of being stored electronically as soil sample data 624. In that embodiment, the soil sample's mass information and moisture information are received via user input (e.g., by a user entering them using an input device (not shown)) so that they can be used by the soil solution preparation module 638 (described below).

The processing server 630 includes various modules such as an extractant calculation module 632 for calculating a needed amount of extractant, a reservoir dispensing module 634 for dispensing a particular amount of extractant and/or cleaning fluid, a mixing module 636 for mixing the contents of the mixing chamber 110, a soil solution preparation module 638 for preparing a soil sample solution with a particular soil-to-extractant ratio, and a cleaning module 639 for cleaning the mixing chamber 110. In one embodiment, the processing server 630 includes a computer (or set of computers) that communicates with repository 620, processes data (e.g., by executing the extraction calculation module 632), and controls the soil analysis device 100 (e.g., by executing the reservoir dispensing module 634, the mixing module 636, the soil solution preparation module 638, and the cleaning module 639).

The extractant calculation module 632 calculates a needed amount of extractant. In particular, the extractant calculation module 632 determines how much extractant should be added to a particular raw soil sample to generate a soil sample solution with a particular soil-to-extractant ratio. In one embodiment, the extractant calculation module 632 calculates the needed amount of extractant as follows:

$M_{dg}=M_{fm}*(100-P_{moisture})/100$ $M_{water}=M_{fm}*P_{moisture}/100$ $M_{extractant}=(R*M_{dg})-M_{water}=(R*M_{fm}*(100-P_{mositure})/100)-(M_{fm}*P_{moisture}/100)$ $V_{extractant}=M_{extractant}/D_{extractant}$ where $M_{extractant}$ represents the mass of extractant needed, $V_{extractant}$ represents the volume of extractant needed, $D_{extractant}$ represents the density of the extractant (for deionized water, $D_{extractant}=1$ g/mL), $M_{fm}$ represents the mass of a field-moist soil sample, $P_{moisture}$ represents the percentage of moisture of a field-moist soil sample, $M_{water}$ represents the mass of water of a field-moist soil sample, $M_{dg}$ represents the dry equivalent mass of a soil sample, and R represents the desired extractant-to-soil ratio (e.g., R=10 means 10:1 extractant-to-soil ratio).

The reservoir dispensing module 634 dispenses a particular amount of extractant and/or cleaning fluid. In particular, the reservoir dispensing module 634 causes a particular amount of extractant and/or cleaning fluid to be moved from the reservoir 130 to the mixing chamber 110. In one embodiment, extractant is moved, and the particular amount of extractant to be moved is equal to the needed amount of extractant calculated by the extractant calculation module 632 to generate a soil sample solution with a particular soil-to-extractant ratio. In another embodiment, cleaning fluid is moved, and the particular amount of cleaning fluid to be moved is equal to the amount of cleaning fluid needed to clean the mixing chamber 110.

Causing a particular amount of extractant and/or cleaning fluid to be moved from the reservoir 130 to the mixing chamber 110 is performed by sending commands to the reservoir air valve 131, the reservoir fill valve 133, the chamber air valve 121, and the compressed air source to begin moving extractant and/or cleaning fluid from the reservoir 130 to the mixing chamber 110 (explained above with reference to FIG. 2). The extractant and/or cleaning fluid flows through the flow meter 134, which measures the flow of the extractant and/or cleaning fluid. The amount of the measured flow is sent from the flow meter 134 to the reservoir dispensing module 634 so that the reservoir dispensing module 634 can determine how much extractant and/or cleaning fluid is being added to the mixing chamber 110. After the proper amount of extractant and/or cleaning fluid has been added to the mixing chamber 110 (as indicated by the flow meter 134), the reservoir dispensing module 634 sends commands to the reservoir air valve 131, the reservoir fill valve 133, the chamber air valve 121, and the compressed air source to cease moving extractant and/or cleaning fluid from the reservoir 130 to the mixing chamber 110.

The mixing module 636 mixes the contents of the mixing chamber 110. In particular, the mixing module 636 sends a command to the mixing assembly 112 to activate the mixing assembly 112, thereby mixing the contents of the mixing chamber 110. In one embodiment, the command causes the mixing assembly 112 to be activated for a predetermined length of time. In another embodiment, the command causes the mixing assembly 112 to remain activated until the mixing assembly 112 receives another command from the mixing module 636, causing the mixing assembly 112 to stop being activated.

The soil solution preparation module 638 prepares, from a particular soil sample, a soil sample solution with a particular soil-to-extractant ratio. In particular, the soil solution preparation module 638 prepares a soil sample solution with the soil-to-extractant ratio indicated in the desired soil-to-extractant ratio 622. Execution of the soil solution preparation module 638 proceeds automatically (i.e., without user intervention) and enables the mixing chamber 110 to be self-filling. In one embodiment, the soil solution preparation module 638 operates as follows:

1. The soil solution preparation module 638 determines the previously-measured mass and moisture content of the particular soil sample. If the mass and moisture content are stored as soil sample data 624, then they are obtained using the particular soil sample's unique identifier. If the mass and moisture content are stored manually (e.g., affixed to the sample container), then they were previously received via user input (e.g., by a user entering them using an input device (not shown)).

2. The soil solution preparation module 638 obtains the desired soil-to-extractant ratio 622. The desired soil-toextractant ratio 622 can be a default value or a previously-received value (e.g., from user input or a file).

3. The soil solution preparation module 638 executes the extractant calculation module 632 to determine how much extractant is needed to prepare, from this particular soil sample, a soil sample solution with the desired soil-to-extractant ratio 622.

4. The soil solution preparation module 638 executes the reservoir dispensing module 634 to dispense a particular amount of extractant (specifically, the amount determined in the previous step) from the reservoir 130 to the mixing chamber 110.

5. The soil solution preparation module 638 executes the mixing module 636 to mix the contents of the mixing chamber 110 (e.g., a raw soil sample and the extractant added in the previous step). The result is a soil sample solution with the desired soil-to-extractant ratio.

The cleaning module 639 cleans the mixing chamber 110. In particular, the cleaning module 639 causes the mixing chamber to be drained of its contents, causes cleaning fluid to be moved from the reservoir 130 to the mixing chamber 110, causes the mixing chamber to be rinsed with the cleaning fluid, and causes the mixing chamber to be dried. Causing these steps to occur is performed by sending commands to the drain box 116, the chamber air valve 121, and the compressed air source 120 (explained above with reference to FIG. 2) and executing the reservoir dispensing module 634 and the mixing module 636. Execution of the cleaning module 639 proceeds automatically (i.e., without user intervention) and enables the mixing chamber 110 to be self-cleaning.

Figure 7:
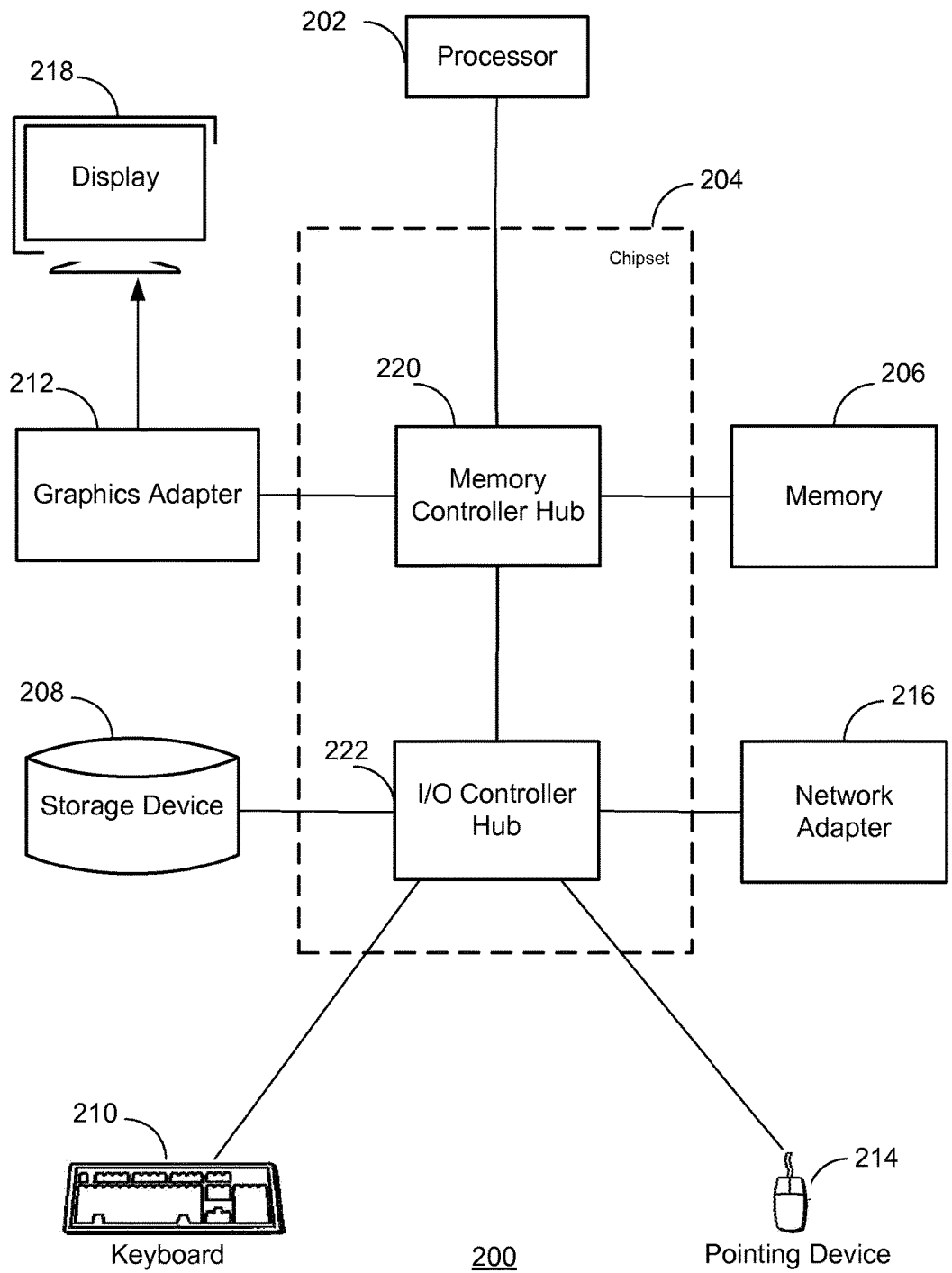
FIG. 7 is a high-level block diagram illustrating an example of a computer for use as a repository and/or a processing server, according to one embodiment.

FIG. 7 is a high-level block diagram illustrating an example of a computer 200 for use as a repository and/or a processing server, according to one embodiment. Illustrated are at least one processor 202 coupled to a chipset 204. The chipset 204 includes a memory controller hub 250 and an input/output (I/O) controller hub 255. A memory 206 and a graphics adapter 213 are coupled to the memory controller hub 250, and a display device 218 is coupled to the graphics adapter 213. A storage device 208, keyboard 210, pointing device 214, and network adapter 216 are coupled to the I/O controller hub 255. A code scanner (e.g., a barcode scanner or RFID scanner, not shown) can also be coupled to the I/O controller hub 255. Other embodiments of the computer 200 have different architectures. For example, the memory 206 is directly coupled to the processor 202 in some embodiments.

The storage device 208 includes one or more non-transitory computer-readable storage media such as a hard drive, compact disk read-only memory (CD-ROM), DVD, or a solid-state memory device. The memory 206 holds instructions and data used by the processor 202. The pointing device 214 is used in combination with the keyboard 210 to input data into the computer system 200. The code scanner (not shown) is used to input data into the computer system 200. The graphics adapter 213 displays images and other information on the display device 218. In some embodiments, the display device 218 includes a touch screen capability for receiving user input and selections. The network adapter 216 couples the computer system 200 to the network 610. Some embodiments of the computer 200 have different and/or other components than those shown in FIG. 7. For example, the repository 620 and/or the processing server 630 can be formed of multiple blade servers and lack a display device, keyboard, and other components.

The computer 200 is adapted to execute computer program modules for providing functionality described herein. As used herein, the term "module" refers to computer program instructions and/or other logic used to provide the specified functionality. Thus, a module can be implemented in hardware, firmware, and/or software. In one embodiment, program modules formed of executable computer program instructions are stored on the storage device 208, loaded into the memory 206, and executed by the processor 202.

Measurement of Soil Characteristics

Before a raw field-moist soil sample is analyzed using the soil analysis device 100, a subsample with known mass and moisture content is prepared. In one embodiment, the subsample is prepared as follows:

1. The raw field-moist soil sample is assigned a unique identifier.

2. The sample is prepared for subsampling by breaking up the cores and larger chunks of dirt so that a subsample of soil can provide representative results of the whole sample. The soil sample can be broken up by hand or automatically (e.g., with a food processor or similar style mixer).

3. A first subsample of soil is taken and placed into a uniquely identified container or batch of containers with a known position. The mass of the subsample is measured by weighing the subsample (either manually or automatically). The mass measurement is stored electronically (in association with the sample's unique identifier) or manually (e.g., by affixing it to the sample container or by manually writing the mass on the container). Determining the mass of a raw soil sample before mixing enables more accurate determination of the concentration of soil nutrients measured by the soil analysis device 100.

4. A second subsample of soil is taken and used to analyze the moisture content of the soil. The moisture content is determined by first weighing the subsample, then drying the subsample (such as with a conventional oven or microwave oven), and then weighing the subsample again. The moisture measurement is stored electronically (in association with the sample's unique identifier) or manually (e.g., by affixing it to the sample container or by manually writing the mass on the container).

Figure 8:
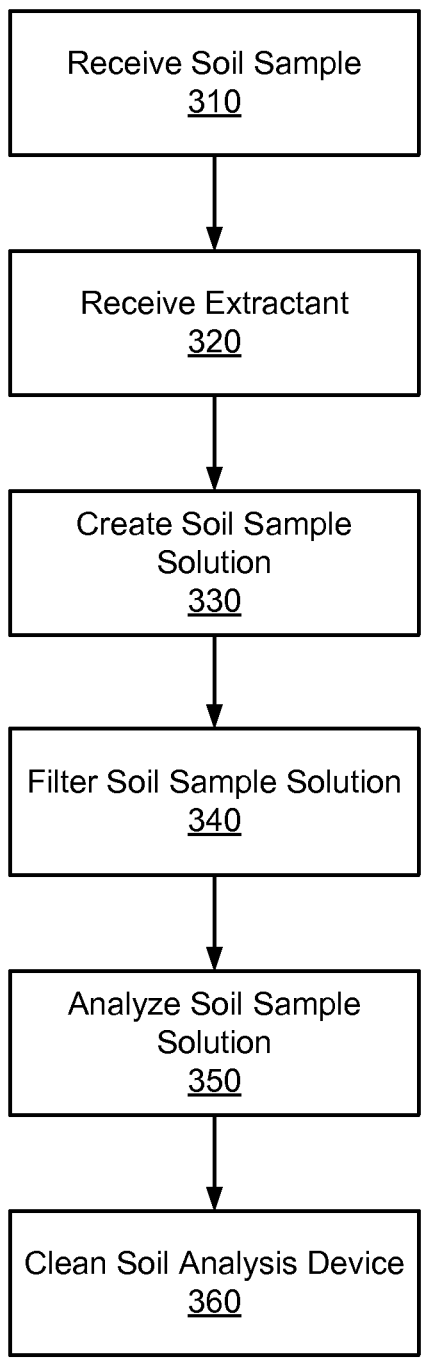
FIG. 8 is a flow chart of a method for analyzing a soil sample solution, according to one embodiment.

FIG. 8 is a flow chart of one embodiment of a method 300 for measuring data describing soil composition using the soil analysis device 100. In the embodiment shown by FIG. 8, the mixing chamber 110 receives 310 a soil sample having a known weight and moisture content. The mixing chamber 110 also receives 320 an extractant. In one embodiment, a volume or weight of extractant is received 320 based on the weight of the soil sample to provide a particular ratio of soil to extractant. The mixing chamber 110 may also receive a salt to act as a flocculent on the soil sample.

The contents of the mixing chamber 110 are mixed to create 330 a soil sample solution. In one embodiment, steps 320 and/or 330 are performed automatically by executing the soil solution preparation module 638. A portion of the soil sample solution flows from the mixing chamber 110 into filtration system 140. The filtration system 140 filters 340 the soil sample solution to remove soil particulates, organic matter, and other soluble organic materials from the soil sample solution. The filtered soil sample solution enters measurement cell 150.

Once in the measurement cell 150, the filtered soil sample solution is analyzed 350 to determine the characteristics of the soil sample. In one embodiment, ultraviolet, visible, and/or near-infrared light are incident upon and at least partially absorbed by the soil sample solution. An attenuation spectrum is measured that provides data regarding how the soil sample solution absorbs different wavelengths of light. Peaks in the attenuation spectrum associated with the soil sample solution allow identification of nutrients, or other components, in the soil sample. A reflection spectrum may also be measured using the light reflected from the soil sample in the measurement cell 150. After measurement, soil analysis device 100 is cleaned 360 to remove the soil sample solution from the mixing chamber 110, filtration system 140, and/or measurement cell 150. In one embodiment, step 360 is performed automatically by executing the cleaning module 639.

Figure 9:
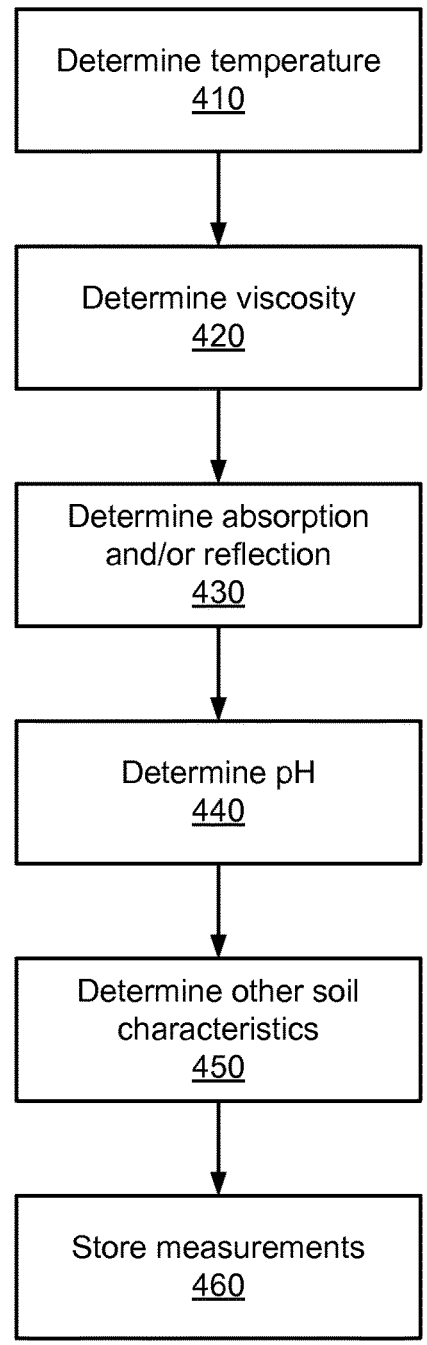
FIG. 9 is a flow chart of a method for capturing multiple types of measurements to determine soil composition, according to one embodiment.

FIG. 9 is a flow chart of one embodiment of a method for analyzing 350 multiple characteristics of a soil sample solution to determine soil sample characteristics. In one embodiment, one or more additional measurement cells 150 are coupled to the mixing chamber 110 and measure various characteristics of a soil sample solution. In one embodiment, measurement cell 150 and one or more additional measurement devices measure various characteristics of the soil sample and the soil sample solution. In one embodiment, measurements of various characteristics of the soil sample solution are measured in a single measurement cell 150, where the contents of the measurement cell 150 may change between measurements for a single soil sample. For example, the soil to extractant ratio may be changed through the addition of additional extractant between measurements, or additional chemicals may be added to perform additional measurements.

In one embodiment, a thermal measurement device determines 410 a temperature of a portion of the soil sample solution. A power detector determines 420 a viscosity of the soil sample solution by measuring the power consumed by the motor in mixing chamber 110 to reach a specified speed, or by measuring the speed of the motor when a fixed amount of power is applied to the motor. In one embodiment, the measurement cell 150 is used to determine 430 an absorption and/or a reflection spectrum of the soil sample solution. In one embodiment an additional measurement device or an additional measurement cell 150 in conjunction with an added chemical determines 440 the pH of the soil.

The temperature, viscosity, attenuation spectrum and pH represent characteristics of the soil. These measurements may also be analyzed to determine other characteristics of the soil that were not directly measured. For example, the temperature, viscosity, attenuation spectrum and pH may be communicated from the soil analysis device 110 to a processor or computing device (not shown) which determines 450 the nutrients present in the soil sample. The measured and determined characteristics of the soil sample are stored 460 in a memory and/or displayed to a user. In one embodiment, the measured and determined characteristics of the soil sample are stored using a computer as described with respect to FIG. 7 above.

In one embodiment, the soil analysis device 100 is used in conjunction with a process for measuring soil characteristics as described in U.S. patent application Ser. No. 13/231, 701, filed on Sep. 13, 2011, the subject matter of which is incorporated herein by reference in its entirety.

Hence, the disclosed soil analysis device 100 improves the accuracy of identifying nutrients in a soil sample while also increasing the speed with which the nutrients included in a soil sample are identified.

Additional Considerations

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. It should be understood that these terms are not intended as synonyms for each other. For example, some embodiments may be described using the term "connected" to indicate that two or more elements are in direct physical or electrical contact with each other. In another example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the invention. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a method for automatically identifying characteristics of the composition of a soil sample through the disclosed principles herein. Thus, while particular embodiments and applications have been illustrated and described, it is to be understood that the present invention is not limited to the precise construction and components disclosed herein and that various modifications, changes and variations which will be apparent to those skilled in the art may be made in the arrangement, operation and details of the method and apparatus of the present invention disclosed herein without departing from the spirit and scope of the invention as defined in the appended claims.

The invention claimed is:

1. A soil analysis device comprising:
   one or more reservoirs configured to store an extractant and/or a cleaning fluid;
   a mixing chamber coupled to the one or more reservoirs and configured to receive the extractant from the one or more reservoirs and to receive raw soil samples;
   a mixing assembly coupled to the mixing chamber and configured to mix contents of the mixing chamber;
   a measurement cell coupled to the mixing chamber and configured to analyze a soil sample solution;
   a drain box coupled to the mixing chamber and configured to evacuate the contents of the mixing chamber; and
   a control system configured to:
      cause the mixing chamber to receive an amount of the extractant from the one or more reservoirs;
      cause the mixing chamber to receive a raw soil sample;

cause the mixing assembly to mix contents of the mixing chamber to produce the soil sample solution;

cause the measurement cell to receive and analyze the soil sample solution;

cause the drain box to evacuate a substantial portion of the soil sample solution from the mixing chamber;

cause the mixing chamber to receive an amount of the cleaning fluid from the one or more reservoirs;

cause the mixing assembly to move the amount of the cleaning fluid within the mixing chamber to clean leftover particulates of the soil sample solution from the mixing chamber; and cause the drain box to evacuate the amount of the cleaning fluid from the mixing chamber.

2. The soil analysis device of claim 1, further comprising:
an air source configured to move the amount of the cleaning fluid from the one or more reservoirs to the mixing chamber;
one or more valves configured to control flow of the amount of the cleaning fluid from the one or more reservoirs to the mixing chamber;
a flow meter configured to measure the amount of the cleaning fluid transferred from the one or more reservoirs into the mixing chamber through the one or more valves; and
wherein the control system is configured to cause the air source to move the amount of the cleaning fluid from the one or more reservoirs to the mixing chamber by:
causing the air source to begin moving the cleaning fluid from the one or more reservoirs to the mixing chamber through the one or more valves;
measuring a flow of the cleaning fluid passing through the one or more valves into the mixing chamber using the flow meter; and
in response to a determination that the flow meter has measured the amount of the cleaning fluid, causing the air source to cease moving the cleaning fluid through the one or more valves.

3. The soil analysis device of claim 2, wherein the control system is further configured to, in response to determining that one or more measurements have been completed, cause the air source to dry the mixing chamber.

4. The soil analysis device of claim 3, wherein the one or more measurements are taken using one or more of: a conductivity probe, a glass pH electrode, or ion selective electrodes.

5. The soil analysis device of claim 3, wherein the one or more measurements include one or more of: determining a moisture content of the soil sample solution, determining a viscosity of the soil sample solution, determining a temperature of the soil sample solution, or determining an amount of one or more elements comprising the soil sample solution.

6. The soil analysis device of claim 2, wherein the control system is configured to cause the air source to move any remaining contents of the mixing chamber through the mixing chamber and the drain box and into a drain line, thereby drying the mixing chamber.

7. The soil analysis device of claim 1, wherein the cleaning fluid comprises deionized water.

8. The soil analysis device of claim 1, wherein the control system is configured to cause the drain box to evacuate the substantial portion of the soil sample solution from the mixing chamber by opening the drain box.

9. The soil analysis device of claim 8, wherein opening the drain box causes the substantial portion of the soil sample solution to be evacuated into a drain line.

10. The soil analysis device of claim 8, wherein the control system is configured to close the drain box after the substantial portion of the soil sample solution has been evacuated.

11. The soil analysis device of claim 1, wherein the control system is configured to move the amount of the cleaning fluid from the one or more reservoirs to the mixing chamber through a spray nozzle that cleans one or more sidewalls of the mixing chamber.

12. The soil analysis device of claim 1, wherein the control system, in response to determining that the mixing chamber has been cleaned, is configured to load a new soil sample into the mixing chamber.

13. The soil analysis device of claim 1, wherein the mixing assembly includes one or more blades attached to a motor.

14. The soil analysis device of claim 13, wherein the motor is connected to a mixing shaft to facilitate mixing the contents of the mixing chamber.

15. The soil analysis device of claim 13, wherein the mixing assembly further includes a turbulence-inducing feature that facilitates the mixing of the contents of the mixing chamber.

16. The soil analysis device of claim 1, wherein the mixing assembly is located at a bottom of the mixing chamber.

17. The soil analysis device of claim 1, wherein the mixing assembly mixes the contents of the mixing chamber through sonication.

18. The soil analysis device of claim 1, wherein the measurement cell comprises one or more optical detectors and an optical source.

19. The soil analysis device of claim 18, wherein the control system is configured to cause the optical source to emit light through the soil sample solution within the measurement cell for detection by the one or more optical detectors, and to cause the one or more optical detectors to capture an attenuation spectrum of the light passing through the soil sample solution and to determine characteristics of the soil sample solution based on the attenuation spectrum.

* * * * *